United States Patent [19]

Mellinger

[11] Patent Number: 4,951,197
[45] Date of Patent: Aug. 21, 1990

[54] WEIGHT LOSS MANAGEMENT SYSTEM
[75] Inventor: Gilbert Mellinger, Jacksonville, Fla.
[73] Assignee: AMC of America, Jacksonville, Fla.
[21] Appl. No.: 309,038
[22] Filed: Feb. 10, 1989

Related U.S. Application Data

[63] Continuation of Ser. No. 864,504, May 19, 1986, abandoned.

[51] Int. Cl.[5] .............................................. G06F 15/42
[52] U.S. Cl. ............................ 364/413.2; 364/413.01
[58] Field of Search ........................... 304/413.29, 567

[56] References Cited

PUBLICATIONS

Nutriplanner 1600 System by Practorcare Corp.
"Programs for a Healthy Practice–Healthaide", M. Schorin, PC Magazine, vol. 3, No. 4, pp. 131–137, 3/6/84, (Abstract).
"Software Gallery: The Original Boston Computer Diet", Run vol. 3, No. 1, pp. 20–22, Jan. 1986 (Abstract).
"Software for Health and Fitness: Marker Control", M.S. Davidson, Creative Computing, vol. 2, No. 3, p. 103, Mar. 1985.
"The Quick Success Program" by Weight Watchers; Participant's brochure.
Nutriplanner 1600 System, Sales brochure.

Primary Examiner—Charles E. Atkinson
Assistant Examiner—Gail O. Hayes
Attorney, Agent, or Firm—Breneman & Georges

[57] ABSTRACT

A weight loss management system utilizes a computer analysis of a participant's past medical history, eating habits, body measurements, exercise level and taste preferences to provide a menu of a specified number of calories to maintain a reasonable weight. The system provides consultation with a dietition in order for a participant to recognize the deficiencies in the past diet. The system further provides consultation to effect behavior modification of the participant by offering instruction in nutrition, exercise and proper cooking techniques.

21 Claims, 11 Drawing Sheets

DAILY MEAL PLANS

| | FRUIT EXCHANGE | MILK EXCHANGE | GRAIN & CEREAL EXCHANGE | FAT EXCHANGE | MEAT EXCHANGE | FRUIT EXCHANGE | VEGETABLE EXCHANGE | MILK EXCHANGE | GRAINS & CEREAL EXCHANGE | FAT EXCHANGE | MEAT EXCHANGE | FRUIT EXCHANGE | VEGETABLE EXCHANGE | MILK EXCHANGE | GRAINS & CEREAL EXCHANGE | FAT EXCHANGE | MEAT EXCHANGE | FRUIT EXCHANGE | MILK EXCHANGE | GRAINS & CEREAL EXCHANGE | FAT EXCHANGE | MEAT EXCHANGE |
|---|---|---|---|---|---|---|---|---|---|---|---|---|---|---|---|---|---|---|---|---|---|---|
| | BREAKFAST ||||| LUNCH ||||||| DINNER ||||||| SNACK |||||
| 1200 CAL. | 1 | — | — | — | — | 2 | 2 | 1 | — | 2 | — | — | 3 | 1 | — | 2 | 2 | 1 | — | — | 1 | — |
| 1500 CAL. | 1 | — | 2 | 2 | — | — | 1 | ½ | 2 | 2 | 2 | — | 1 | ½ | 2 | 2 | 2 | 1 | 1 | — | — | — |
| 1800 CAL. | 2 | 1 | 2 | 3 | 2 | 1 | 2 | 1 | 3 | 3 | 2 | 1 | 2 | 1 | 2 | 3 | 2 | 1 | ½ | 1 | 1 | — |
| 2100 CAL. | 1 | 1 | 3 | 4 | 2 | 2 | 2 | 1 | 2 | 3 | 3 | 2 | 2 | 1 | 2 | 4 | 2 | 1 | ½ | — | — | — |
| 2400 CAL. | 2 | 1 | 2 | 4 | 2 | 2 | 3 | 1 | 3 | 3 | 3 | 2 | 3 | 1 | 3 | 3 | 3 | 1 | 1 | 2 | — | — |

| FRUIT EXCHANGE | VEGETABLE EXCHANGE | MILK EXCHANGE | GRAIN AND CEREAL EXCHANGE |
|---|---|---|---|
| ONE EXCHANGE | ONE EXCHANGE = 1/2 CUP | ONE EXCHANGE | ONE EXCHANGE |
| PROTEIN (0g.) FAT (0g.) CARBO. (10g.) CALORIES (40) | PROTEIN (2g.) FAT (0g.) CARBO. (5g.) CALORIES (25) | PROTEIN (8g.) FAT (0g.) CARBO. (12g.) CALORIES (80) | PROTEIN (2g.) FAT (0g.) CARBO. (15g.) CALORIES (70) |
| APPLE, 1 SMALL APPLE JUICE, 1/3 CUP APPLESAUCE, 1/2 CUP APRICOTS, 2 BANANA 1/2 MEDIUM BERRIES, 1/2 CUP CANTALOUPE, 1/4 CHERRIES, 10-12 CRANBERRY JUICE, 1/4 CUP FIG, 1 FRUIT SALAD, 1/2 CUP GRAPES, SEEDLESS 10 GRAPEFRUIT, 1/2 MEDIUM * GRAPEFRUIT JUICE, 1/2 CUP * HONEYDEW MELON, 1/4 SMALL MANGO, 1/2 SMALL ORANGE, 1 SMALL * ORANGE JUICE, 1/2 CUP * PAPAYA, 1/2 SMALL PEACH, 1 MEDIUM OR 1/2 CUP SLICES PEAR, 1/2 SMALL PINEAPPLE, 1/2 CUP PLUMS, 2 RAISINS, 2 Tbs. STRAWBERRIES, 1 CUP* TANGERINE, 1 WATERMELON, 1 CUP | ASPARAGUS * BEANS, GREEN & YELLOW BEETS BROCCOLI * CABBAGE CARROTS * CAULIFLOWER CELERY COLLARD GREENS * CUCUMBERS EGGPLANT KALE * MUSHROOMS OKRA * ONIONS RHUBARB RUTEBAGA RADISHES SAUERKRAUT SCALLIONS SPINACH * SUMMER SQUASH * TURNIP GREENS * TOMATOES TURNIPS ZUCCHINI | BUTTERMILK, 1 CUP CHEESE (SEE MEAT EXCHANGE MILK, LOW FAT 2% 1 CUP (OMIT 1 FAT EXCHANGE) MILK, SKIM, 1 CUP MILK, WHOLE, 1 CUP (OMIT 2 FAT EXCHANGES) YOGURT, SKIM OR LOWFAT PLAIN, 1 CUP (OMIT 1/2 FAT EXCHANGE) | BAGEL, SMALL 1/2 (1 oz) BREAD, ANY TYPE, 1 SLICE (1 oz) BISCUIT, 1 SMALL CEREAL (COLD), 3/4 oz. CEREAL (HOT), 3/4 oz. DRY OR 1/2 CUP, COOKED CORNBREAD, 1 2" SQUARE CORN, 1/2 CUP CRACKERS, 3 ENGLISH MUFFIN 1/2 (1 oz.) GRITS, 1/2 CUP COOKED LIMA BEANS, 1/2 CUP MELBA TOAST, 6 ROUNDS OR 4 SLICES PASTA, 1/2 CUP PEAS, 1/2 CUP PITA, 1 oz. POPCORN, 3 CUPS, POPPED, PLAIN POTATO, 1 SMALL RICE, 1/2 CUP COOKED SALTINES, 5 TORTILLA, 9" DIAM. |

\* THESE VEGETABLES ARE GOOD SOURCES OF VITAMIN A. SELECT AT LEAST ONE DAILY.

\* THESE FRUITS ARE GOOD SOURCE OF VITAMIN C. SELECT AT LEAST 1 DAILY.

| FAT EXCHANGE | LEAN MEAT/ALT. EXCHANGE | MEDIUM FAT MEAT*/ALT. EXCHANGE | HIGH FAT MEAT*/ALT. EXCHANGE |
|---|---|---|---|
| ONE EXCHANGE | ONE EXCHANGE | ONE EXCHANGE | ONE EXCHANGE |
| PROTEIN (0g.)<br>FAT (5g.)<br>CARBO. (0g.)<br>CALORIES (45) | PROTEIN (7g.)<br>FAT (3g.)<br>CARBO. (0g.)<br>CALORIES (55) | PROTEIN (7g.)<br>FAT (5.5g.)<br>CARBO. (0g.)<br>CALORIES (75) | PROTEIN (7g.)<br>FAT (8g.)<br>CARBO. (0g.)<br>CALORIES (100) |
| BACON, CRISP<br>  1 SLICE<br>BUTTER, 1 tsp.<br>CREAM, HEAVY,<br>  1 Tbs.<br>CREAM, LIGHT,<br>  2 Tbs<br>CREAMCHEESE,<br>  1 Tbs.<br>MARGARINE, 1 tsp.<br>MAYONNAISE,<br>  1 tsp.<br>NON-DAIRY<br>  CREAMER<br>  3 Tbs.<br>NUTS:<br>  ALMONDS, 10<br>  PEANUTS, 10<br>  PISTACHIOS, 20<br>  OTHER NUTS,<br>    5 To 6<br>OLIVES, GREEN<br>  10 LARGE<br>SALAD DRESSING,<br>  1 Tbs.<br>SOUR CREAM<br>  2 Tbs.<br>VEGETABLE OIL,<br>  1 tsp. | BEEF, 1 oz.:<br>  CHUCK<br>  FLANK STEAK<br>  PLATE RIBS<br>  TENDERLOIN<br>CHEESE, SKIM,<br>  1 oz.<br>COTTAGE CHEESE,<br>  1/4 CUP DRY &<br>  2% BUTTERFAT<br>DRIED BEANS, 1/2<br>  CUP COOKED *<br>FISH, 1 oz.:<br>  SALMON<br>  TUNA<br>  CRAB<br>LAMB, 1 oz.<br>PORK, 1 oz. CENTER<br>  SLICE HAM<br>POULTRY, 1 oz.:<br>  CHICKEN<br>  TURKEY<br>  CORNISH HEN<br>SHELLFISH, 5:<br>  SHRIMP<br>  OYSTERS<br>  SCALLOPS<br>VEAL, 1 oz.:<br>  CUTLETS<br>  LEG<br>  LOIN<br><br>* WHEN CHOOSING,<br>  OMIT ONE BREAD<br>  EXCHANGE | BEEF, 1 oz.:<br>  GROUND<br>  (15% FAT)<br>  CORNED BEEF<br>  GROUND ROUND<br>  RIB EYE<br>CHEESE, PART<br>SKIM, 1 oz.:<br>  MOZZARELLA<br>  RICOTTA<br>  PARMESAN<br>EGG, 1 <br>PEANUT BUTTER,<br>  1 Tbs. (OMIT 2<br>  FAT EXCHANGES)<br>PORK, 1 oz.:<br>  NECK BONES<br>  CANADIAN<br>  BACON<br>  BOSTON BUTT<br>POULTRY, 1 oz.:<br>  CAPON<br>  DUCK<br>VARIETY MEATS,<br>  1 oz.:<br>  LIVER<br>  KIDNEY<br>  SWEETBREADS<br><br>* WHEN CHOOSING<br>  OMIT 1/2 FAT<br>  EXCHANGE.<br>** RICH IN<br>  CHOLESTEROL. | BEEF, 1 oz.:<br>  BRISKET<br>  HAMBURGER<br>  RIB ROASTS<br>CHEESE, WHOLE<br>  MILK, 1 oz<br>  CHEDDAR TYPES<br>COLD CUTS, 1 oz.:<br>  BOLOGNA<br>  MINCED HAM<br>  SALAMI<br>FRANKFURTER,<br>  1 SMALL<br>PORK, 1 oz.:<br>  LOIN<br>  GROUND PORK<br>  PIG FEET<br>  MINCED HAM<br>POULTRY, 1 oz.:<br>  GOOSE<br><br>* WHEN CHOOSING,<br>  OMIT 1 FAT<br>  EXCHANGE |

NUTRITIONAL ANALYSIS

| NUTRIENT | AVERAGE DAILY INT. | MAXIMUM DAILY INT. | MINIMUM DAILY INT. | (STANDARD DEVIATION) MEAL | DAY | R.D.A. ALLOWANCE | CALCULATED BASIS ALLOWANCE | PERCENT | /EXCESS |
|---|---|---|---|---|---|---|---|---|---|
| WATER PERCENTAGE | 0.00 | 0.00 | 0.00 | 383.18 | 0.00 | 0.00 | 0.00 NONE | 0.0 | +0.00 |
| CALORIES | 1,770.37 | 1,770.37 | 1,770.37 | 447.17 | 0.00 | 1,540.00 | 1,540.00 R.D.A. | 115.0 | +230.37 |
| PROTEIN | 80.83 | 80.83 | 80.83 | 21.09 | 0.00 | 46.00 | 50.91 MAX AMT | 158.0 | +34.82 |
| FAT | 54.25 | 54.25 | 54.25 | 13.96 | 0.00 | 66.00 | 66.00 MAX AMT | 82.2 | -11.75 |
| CARBOHYDRATE | 238.93 | 238.93 | 238.93 | 59.73 | 0.00 | 300.00 | 300.00 MAX AMT | 79.6 | -61.07 |
| FIBER | 4.53 | 4.53 | 4.53 | 1.61 | 0.00 | 7.00 | 7.00 R.D.A. | 45.3 | -2.47 |
| ASH | 15.61 | 15.61 | 15.61 | 4.08 | 0.00 | 0.00 | 0.00 NONE | 0.0 | +0.00 |
| CALCIUM | 283.45 | 283.45 | 283.45 | 71.61 | 0.00 | 800.00 | 800.00 R.D.A. | 35.4 | -516.55 |
| PHOSPHORUS | 884.30 | 884.30 | 884.30 | 221.74 | 0.00 | 800.00 | 800.00 R.D.A. | 110.5 | +84.30 |
| IRON | 15.25 | 15.25 | 15.25 | 4.11 | 0.00 | 18.00 | 18.00 R.D.A. | 84.7 | -2.75 |
| SODIUM | 3,619.73 | 3,619.73 | 3,619.73 | 916.82 | 0.00 | 1,100.00 | 1,100.00 MAX AMT | 109.7 | 2,519.73 |
| POTASSIUM | 2,296.53 | 2,296.53 | 2,296.53 | 718.11 | 0.00 | 1,875.00 | 1,875.00 R.D.A. | 122.5 | +421.53 |
| VITAMIN A | 1,658.53 | 1,658.53 | 1,658.53 | 432.79 | 0.00 | 5,000.00 | 5,000.00 R.D.A. | 33.2 | -3,341.47 |
| THIAMIN | 1.31 | 1.31 | 1.31 | 0.35 | 0.00 | 1.00 | 1.00 R.D.A. | 130.7 | +0.31 |
| RIBOFLAVIN | 1.18 | 1.18 | 1.18 | 0.33 | 0.00 | 1.20 | 1.20 R.D.A. | 98.5 | -0.02 |
| NIACIN | 23.50 | 23.50 | 23.50 | 5.96 | 0.00 | 13.00 | 13.00 R.D.A. | 180.8 | +10.50 |
| VITAMIN C | 61.38 | 61.38 | 61.38 | 24.33 | 0.00 | 60.00 | 60.00 R.D.A. | 102.3 | +1.38 |
| SATUR'D FATTY ACI | 18.38 | 18.38 | 18.38 | 4.70 | 0.00 | 0.00 | 0.00 NONE | 0.0 | +0.00 |
| OLEIC ACID | 17.10 | 17.10 | 17.10 | 4.63 | 0.00 | 0.00 | 0.00 NONE | 0.0 | +0.00 |
| LINOLEIC ACID | 12.35 | 12.35 | 12.35 | 3.09 | 0.00 | 0.00 | 0.00 NONE | 0.0 | +0.00 |
| CHOLESTEROL | 478.00 | 478.00 | 478.00 | 148.64 | 0.00 | 300.00 | 300.00 MAX AMT | 159.3 | +178.00 |
| REFUSE FACTOR | 19.30 | 19.30 | 19.30 | 5.25 | 0.00 | 0.00 | 0.00 NONE | 0.0 | +0.00 |
| ALCOHOL | 0.00 | 0.00 | 0.00 | 0.00 | 0.00 | 0.00 | 0.00 NONE | 0.0 | +0.00 |

FIG. 8

CHOOSING THE RIGHT MEAL PLAN

REASONABLE WEIGHT TABLES

WEIGHT IN POUNDS ACCORDING TO FRAME, INCLUDING INDOOR CLOTHING WEIGHING 5 lbs. FOR MEN, 3 lbs. FOR WOMEN.

HEIGHT INCLUDES SHOES WITH 1" HEELS

HOW MANY CALORIES SHOULD I CONSUME DAILY TO MAINTAIN MY REASONABLE WEIGHT ?

PICK YOUR REASONABLE WEIGHT ______

MULTIPLY BY 11 FOR SEDENTARY x ______
ACTIVITY
13 FOR LIGHT ACTIVITY
15 FOR MODERATE ACTIVITY
20 FOR STRENUOUS ACTIVITY

THE NUMBER OF CALORIES NEEDED TO MAINTAIN REASONABLE WEIGHT = ______

EXAMPLE:
MY WEIGHT IS          140 lbs.
ACTIVITY LEVEL IS  x   13
   LIGHT

CALORIES NEED TO MAINTAIN
REASONABLE WEIGHT  =  1820

YOU WOULD THEN PICK AN 1800 CALORIE MEAL PLAN

| HEIGHT MEN | SMALL FRAME | MEDIUM FRAME | LARGE FRAME |
|---|---|---|---|
| 5'2" | 128-134 | 131-141 | 138-150 |
| 5'3" | 130-136 | 133-143 | 140-153 |
| 5'4" | 132-138 | 135-145 | 142-156 |
| 5'5" | 134-140 | 137-148 | 144-160 |
| 5'6" | 136-142 | 139-151 | 146-164 |
| 5'7" | 138-145 | 142-154 | 149-168 |
| 5'8" | 140-148 | 145-157 | 152-172 |
| 5'9" | 142-151 | 148-160 | 155-176 |
| 5'10" | 144-154 | 151-163 | 158-180 |
| 5'11" | 146-157 | 154-166 | 161-184 |
| 6' | 149-160 | 157-170 | 164-188 |
| 6'1" | 152-164 | 160-174 | 168-192 |
| 6'2" | 155-168 | 164-178 | 172-197 |
| 6'3" | 158-172 | 167-182 | 176-202 |
| 6'4" | 162-176 | 171-187 | 181-207 |
| WOMEN | | | |
| 4'10" | 102-111 | 109-121 | 118-131 |
| 4'11" | 103-113 | 111-123 | 120-134 |
| 5' | 104-115 | 113-126 | 122-137 |
| 5'1" | 106-118 | 115-129 | 125-140 |
| 5'2" | 108-121 | 118-132 | 128-143 |
| 5'3" | 111-124 | 121-135 | 131-147 |
| 5'4" | 114-127 | 124-138 | 134-151 |
| 5'5" | 117-130 | 127-141 | 137-155 |
| 5'6" | 120-133 | 130-144 | 140-159 |
| 5'7" | 123-136 | 133-147 | 143-163 |
| 5'8" | 126-139 | 136-150 | 146-167 |
| 5'9" | 129-142 | 139-153 | 149-170 |
| 5'10" | 132-145 | 142-156 | 152-173 |
| 5'11" | 135-148 | 145-159 | 155-176 |
| 6' | 138-151 | 148-162 | 158-179 |

FIG. 9

WEIGHT LOSS MANAGEMENT SYSTEM

This application is a continuation of application Ser. No. 864,504, filed May 19, 1986.

BACKGROUND OF THE INVENTION

The present invention is directed to a weight management system which educates the participant in nutrition and in developing a lifestyle necessary to reach and consistently maintain one's weight. More particularly the invention provides an analysis of physical parameters, past eating and exercise habits and taste preferences to determine an individualized weight loss program specifically for an individual.

It is well known that a large percentage of the population is overweight or is prone to be overweight and constantly trying to lose weight by experimenting with various diet programs to reduce their caloric and carbohydrate intake. In addition to diet programs there are numerous dietetic foods, drugs, weight reduction programs and machines offered to aid people in reducing their weight.

In studying the overweight population the medical field is generally of the opinion that an effective method of controlling weight requires the balance of the amount of food consumed with the amount of exercise a person is involved in. When an imbalance occurs and there is a greater intake of calories than required for the amount of energy expended in the average day, an increase in weight occurs. Maintaining a reasonable balance between the caloric intake and the energy expended during the day is necessary in order to lose weight and maintain a constant weight.

Numerous charts and publications have been provided to give accurate data on the caloric content of foods and beverages. In addition, charts have been assembled to provide information on the numbers of calories burned for particular activities and particularly for light and strenuous exercise. Many individuals have successfully attained their desired weight and been able to maintain that weight by balancing the caloric intake with the amount of exercise they average during the week.

One of the more common approaches to losing weight is to obtain a book or chart which lists the number of calories per serving of particular food items. The dieter then resorts to looking up food items at each meal to determine whether that food item should be consumed and if so how much. The dieter must then accurately record what has been consumed and the activities performed throughout the entire day in order to control the daily intake of calories. To be truly effective, data of this type must be accurate and must b continuously accounted for 24 hours every day. This inconvenience most likely is responsible for the fact that only a relatively small number of persons use this technique, even though it is an effective solution to the problem of weight control.

To ease the burden of record taking, hand-held calculators have been proposed which maintain a running balance of calories consumed thoughout the day. Some of these calculators, for example U.S. Pat. No. 4,244,020 to Ratcliff, provide a memory for the number of calories in a serving of particular items. Thus the dieter enters a code corresponding to a particular food item and the calculator records the number of calories and food. This enables the dieter to maintain a running balance of food consumed throughout the day.

Many of these proposed diet programs are defficient in that they fail to account for the sources of calorie intake and the different nutritional values each food item supplies. These programs are generally intended to fit a wide range of individuals which often work for some people but do not provide satisfactory results for others. Thus there is a constant debate as to which is the best and most effective diet for weight loss and maintaining a desired weight. Many dieters attempt to take nutritional factors into account when planning a meal but this planning oftentimes is undertaken with inadequate knowledge and requires a greater amount of discipline and mental effort than the dieter is able to put forth. None of the known weight loss programs take into account the amount of exercise a person normally gets during the day and tailors the diet according to that amount of exercise while at the same time taking into account nutritional values of the food, the source of the calories and the taste preferences of the individual.

The selection of foods offered by the diet are usually quite limited. Dieters tend to select only a few preferred items from the accepted list which makes the diet rapidly become boring and monotonous. Additionally, the narrow selection of foods offered or selected results in skipping meals or having meals tending not to be nutritionally balanced. Medical specialists are of the firm belief that this is not a healthy and effective manner in which to control weight.

Thus a serious need exists for a weight management system which can be tailored to the individual to accommodate for the amount of exercise, the number of calories required to maintain a desired weight and the taste preferences of the individual. There is further a need for a weight managing system which is healthy and enjoyable such that the participant will stay with the program for a length of time necessary to initially lose the desired weight and will also continue to follow the system to maintain that weight. Past weight loss programs have not provided for the specific needs of the individual. None of these programs provide a detailed analysis of the participants past history including their level of exercise normally encountered and comparing it with their physical characteristics and taste preferences for foods. Such an analysis would allow the development of a customized program for the individual to enable them to comfortably alter their lifestyle and eating habits thereby losing and maintaining a desired weight.

SUMMARY OF THE INVENTION

The present invention relates to a weight management system which enables a participant to lose and maintain a desired weight without crash dieting. More specifically, the invention provides a system which compensates for the specific needs, characteristics and taste preferences of a participant, enabling comfortable alteration of lifestyle while maintaining a proper balance of exercise, nutrition and calorie intake.

The system according to the present invention provides a satisfactory and successful way to alter a participant's lifestyle. The system educates participants in eating a correct amount of proper foods, proper cooking procedures for the foods and the proper amount and kind of exercise needed. The system takes into account numerous considerations including the physical health and the family and work situation of the participant. In order to have an effective weight loss system it is essential that each of these factors be considered and accounted for. Proper eating habits demand that not only certain foods be eaten but that different sources of foods be consumed in proper proportions.

The system utilizes a computer analysis of various parameters to determine the strength and weaknesses of a participant's present diet, exercise program and cooking techniques. The parameters considered in the analysis include the participant's present diet and calorie consumption, physical health, sex, age, height and build. This information is put into the computer and compared with an ideal weight for the participant's height and build. In analyzing the information a determination is made for the individual for the daily intake requirements in order to reach a desired weight and to maintain that weight. A series of charts is produced indicating the variations between the participant's past diet and a recommended diet. The first chart is a bar graph indicating the excess and deficiencies of the recommended daily requirements of various vitamins and nutrients. A second chart is a comparison between the participant's source of calories and the source of calories of a recommended diet. These charts provide the participant with information indicating the deficiencies in the present diet.

The system provides a complete weight loss program by providing counseling and behavior modification in the form of alternatives to present eating, cooking and exercise habits. Different goals are set for the individual to sequentially correct each of the deficiencies indicated in the analysis. For example, if a high sodium content appears in the chart the counselors work with the individual to adjust their diet to reduce the salt intake by that excessive amount indicated. Periodic consultations are performed to ascertain whether the participant has reached the goal desired. At this point if the goal has been reached a second goal to correct a further deficiency is set.

The participant is provided with cooking demonstrations and instructions to teach proper methods of low calorie cooking and how to prepare nutritional and satisfying meals. Each participant receives a Food Exchange Chart from which to select food items and organize meals. The Food Exchange Chart is broken down into the various food categories, listing under each category numerous food items from which the participant may choose. This enables the participant to have variety in their diet and to select according to their taste preferences. A Daily Meal Plan chart indicates maximum calorie per day diets. For each of these diets the quantity of each food item is indicated which is necessary to maintain the maximum calorie per day diet.

The meal plans are based on an individual's need and the deficiencies in their previous eating habits. The system according to the present invention provides meals where the calories and vitamins come from each of the various food categories of the Food Exchange Chart. The system provides that the source of protein, vitamins and calories is equally as important as the quantity. The meal plans provided under the system require specified amounts of food items from each category of the food chart. Accordingly the system requires a specified daily intake of fruit, milk, grain, vegetable, fat and meat.

As with any diet program, exercise plays an important part. The present weight management system as part of the behavior modification offers exercise charts to educate the participant in proper exercise procedures and the amount of exercise needed. Counseling is offered to provide positive reinforcement for the exercise program and to aid the participant in adjusting to the new lifestyle.

Brief Description of the Drawings

The invention will be further described in conjunction with the following drawings in which:

FIG. 8 is a Nutritional Analysis Report of nutrients.

FIG. 9 is a Reasonable Weight Table for weights of men an women.

Description Of The Preferred Embodiment

Figure 1A:
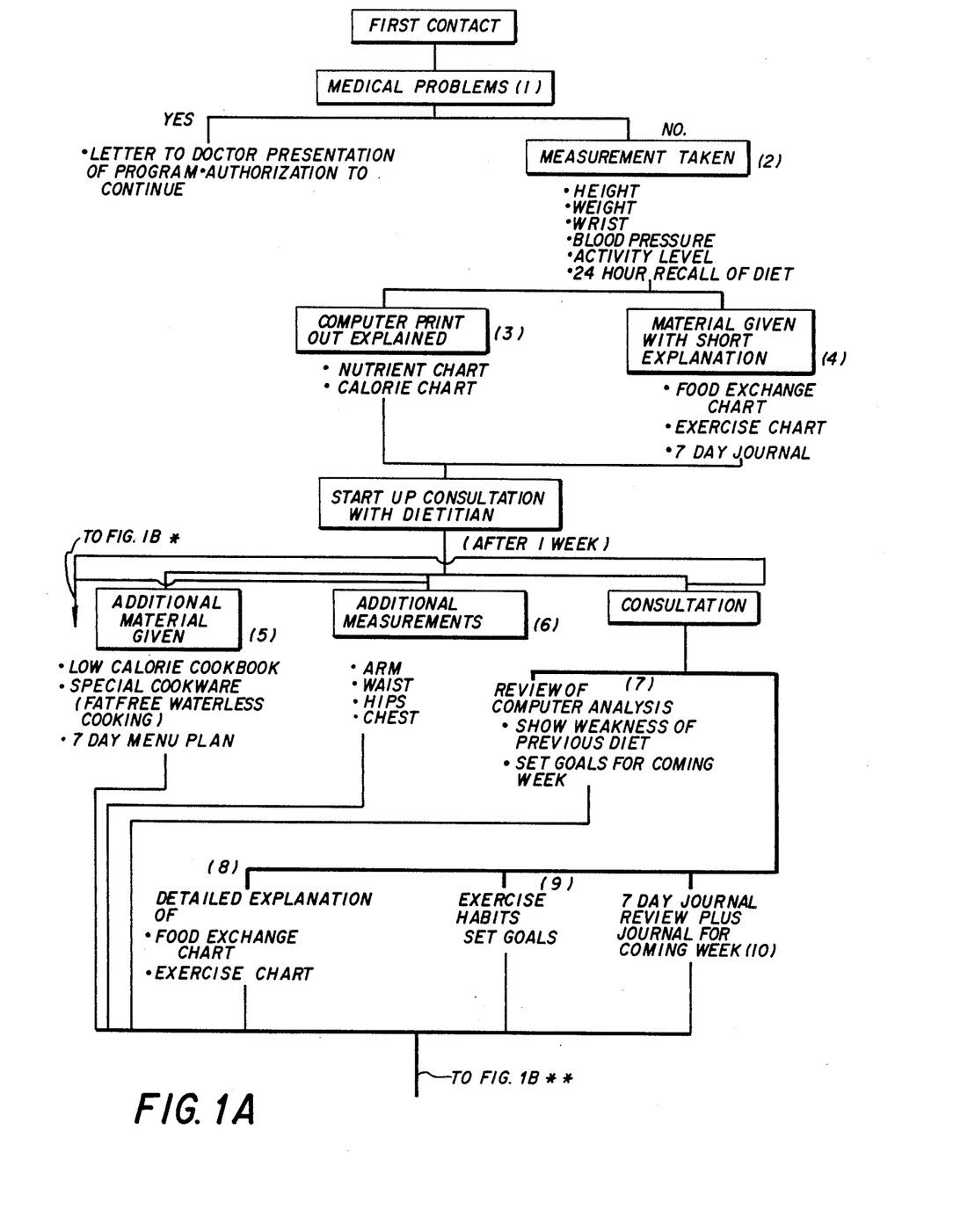
FIGS. 1A and 1B are block diagrams of the weight management system.
Figure 1B:
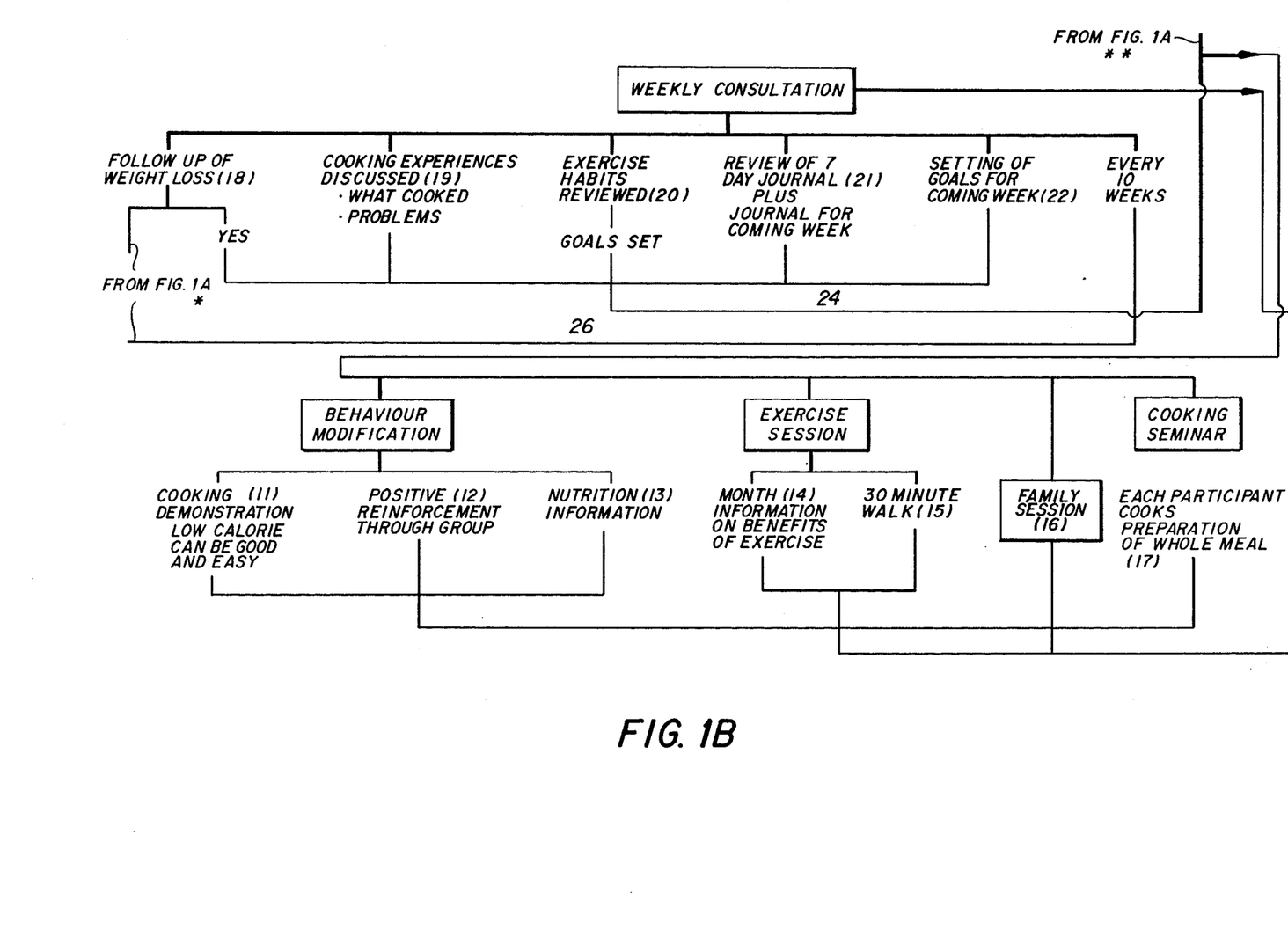

Referring to FIG. 1, there is shown in overall scope a system operational flow chart for implementing the weight management system incorporating the principles of the present invention. The system is a personalized management program which can be divided into two main building blocks. The first building block provides individual personal contact with the participant, offering initial and weekly consultations. The second essential building block is a group program with other participants in behavior modification, exercise sessions, family sessions and cooking instructions.

Once contact has been made with the participant a thorough record is made of the medical history as indicated by functional block 1. This history includes blood pressure, chronic diseases, present weight, height, present physical health, whether the participant is diabetic, etc. If the health of the participant is found unsatisfactory the counselor will require a full medical exam and receipt of a written authorization from a doctor to continue with the weight management system.

If the physical health is found to be satisfactory a series of measurements are taken as indicated by functional block 2. These measurements provide information to accurately develop a proper weight management system. Additionally these measurements provide a reference point to determine whether the system is effective. The measurements include height, weight, blood pressure, as well as measurements of the wrist, upper arms, chest, waist, hips, thighs and finger. In preparing an individual weight loss program it is essential to consider the present physical activity level and diet of the participant. Each of the above parameters is entered into a computer to analyze the participant's eating habits. The analysis by the computer is the basic tool from which the assessment can be made by the dietitian or counselor. In addition, this analysis provides the participant with information to recognize the required changes in eating habits.

The computer analysis 3 consists of two charts for review by the participant and the dietitian. The first chart is a nutrient chart shown in FIG. 2. This chart is in the form of a bar graph with percentages ranging from 0 to 200 in the vertical axis. The hundred percent line drawn horizontally across the graph represents the recommended daily requirements. Spaced along the horizontal axis are bars indicating a plurality of vitamins and nutrients. The bars extend upwardly to indicate the amount of vitamins and nutrients consumed during an average day in comparison with the recommended allowance. The graph thus gives a clear indication of deficiencies and excessive amounts of vitamins and nutrients consumed in the present diet.

Figure 3:
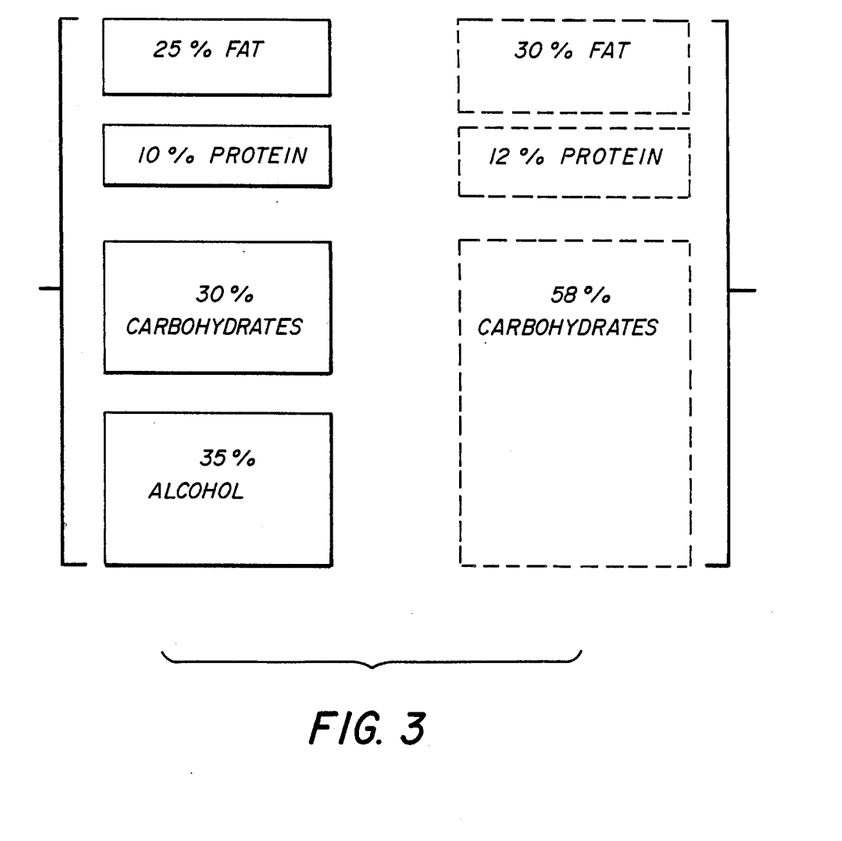
FIG. 3 is a comparison chart between the sources of calories in a present diet and the recommended sources.

The second chart of the computer analysis as shown in FIG. 3. Here the source of the calories are identified as coming from fats, protein, carbohydrates and alcohol. The respective percentages from each group is shown in comparison with a similar chart of recommended percentages of calorie intake. This comparison provides to the dietitian and the participant a clear indication of deficiencies in the source of calories and the need to reduce calorie intake from other sources. The charts are primarily prepared for the benefit of the dietitian to aid in preparing a meal plan and for the benefit of the participants to aid in setting goals in altering the eating habits.

As an additional part of the computer analysis a Nutrition Analysis Report is prepared as shown in FIG. 8. This report, prepared solely for use by a dietition, lists a daily average intake of numerous nutrients. Columns adjacent the Average Daily Intake report the maximum and minimum daily intake and the standard duration per meal and per day. This gives the dietitian an indication of an inconsistent diet by the participant and the need to correct the existing eating habits. An additional column lists the Recommended Daily Allowance as recommended by the U.S. Senate Committee. From this data the percentage of nutrient intake compared to the Recommended Daily Allowance is calculated and printed on the report. Finally a column reporting the deficiency or excess of nutrients consumed appears. From this column the dietitian can readily identify those nutrients of which the participant's diet suffers a deficiency.

Referring to FIG. 8 the participant's Nutrition Analysis Report in this example is from data recorded for a single day. For this reason the Average Daily Intake, The Maximum Daily Intake and the Minimum Daily Intake are identified. If the Report is prepared from, for example, data of an entire week there would of course be a Maximum and a Minimum Daily Intake which differs from the Average Daily Intake. When data is included spanning the food consumption over several days a Standard Deviation for each day can be calculated using standard statistical analysis. The analysis of the participant's previous diet as shown in FIG. 8 reveals that the calorie intake is 115% of the Recommended Daily Allowance or in an excess of 230.37 calories per day. The participant's fat intake, however, in only 82% of the Recommended Daily Allowance resulting in a deficiency of 11.75 grams per day. A similar situation occurs in the carbohydrates intake which is deficient by 61.07 grams per day. This Nutritional Analysis Report is thus a valuable tool in the analysis a participant's previous diet and determining which phases of the diet need particular attention.

Figure 2:
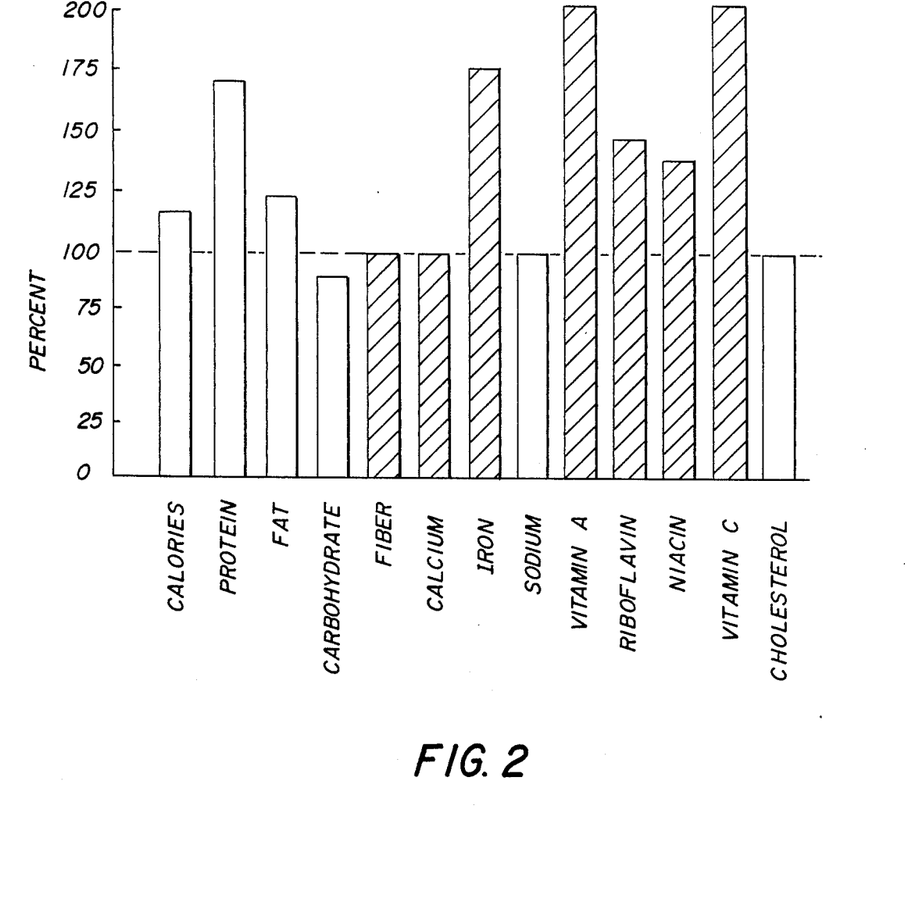
FIG. 2 is a comparison between sources of calorie intake and recommended sources of calorie intake.
Figure 7:
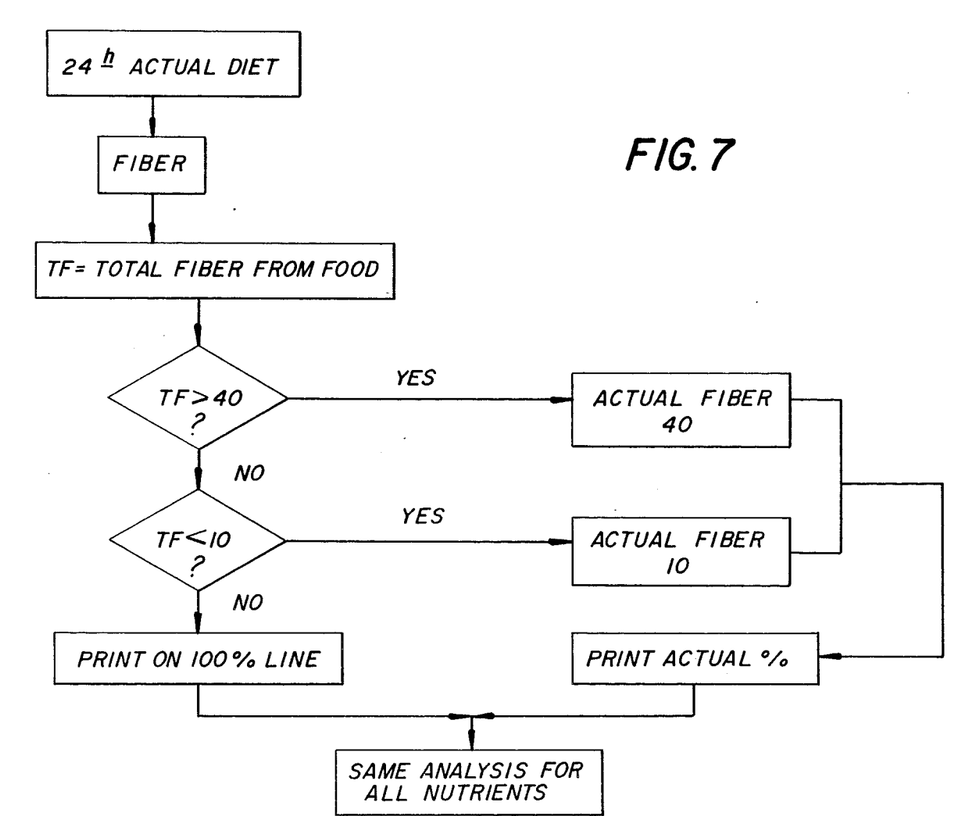
FIG. 7 is a flow diagram of the computer analysis calculating percentages of nutrients in a diet.

In determining the percentages of nutrients compared to the recommended daily allowance the computer goes through a series of determinations as shown in FIG. 7. The flow chart of FIG. 2 represents the thought process of the analysis using fiber intake as an example. From the actual diet the computer through stored information is able to determine the amount of fiber in each food item. The generally accepted range of fiber intake is from 10–40 grams per day. The computer initially determines if the daily fiber intake is in excess of the maximum 40 grams/day allowance. If the fiber intake does not exceed 40 grams the total fiber intake is divided by 40 to calculate the percentage fiber over the maximum allowed amount which is printed on the bar graph of FIG. 2. If the fiber intake does not exceed 40 grams/day the computer then determines if the fiber intake is greater than 10 grams/day. If the fiber intake is greater than 10 grams/day and less than 40 grams/day the computer will print the fiber on the bar graph of FIG. 2 at the 100% line indicating that the fiber intake is within the acceptable level. Should the fiber intake be less than 10 grams/day the total fiber intake is divided by 10 to calculate the percentage of fiber in the daily diet. A similar analysis is performed by the computer for each of the nutrients.

Figure 4:
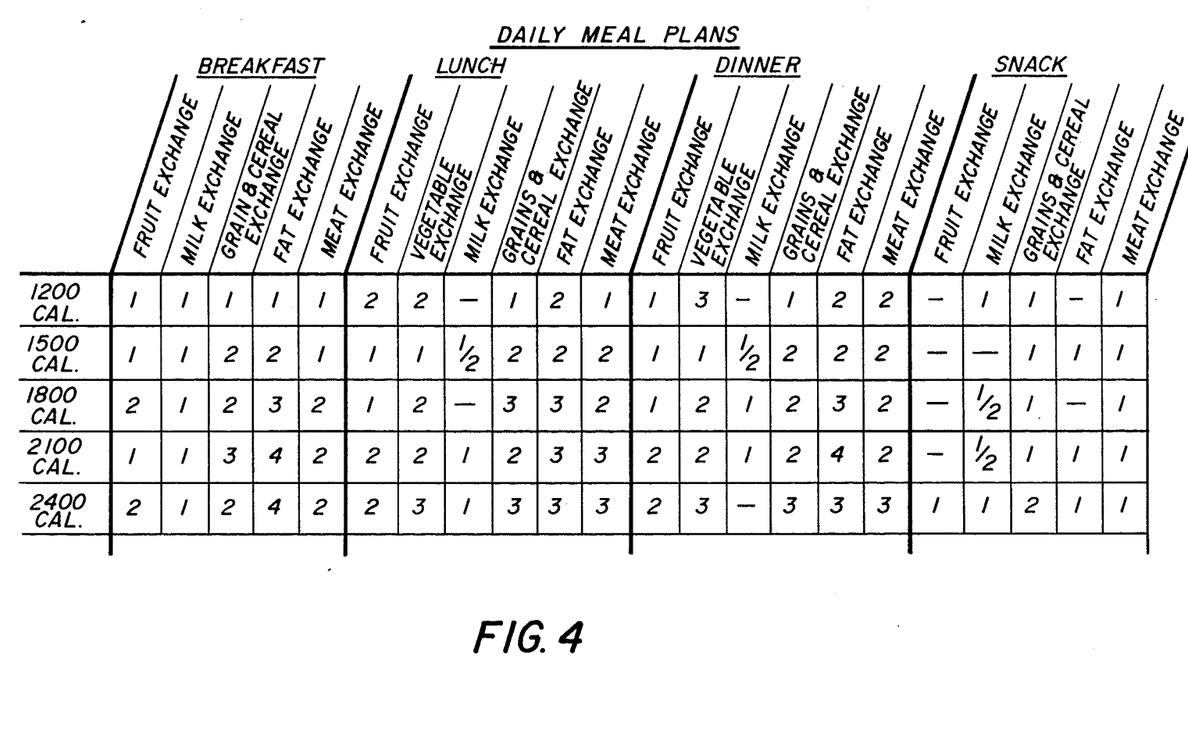
FIG. 4 is a food chart indicating the quantity of food items for a maximum calorie per day diet.
Figures 5, 5A:
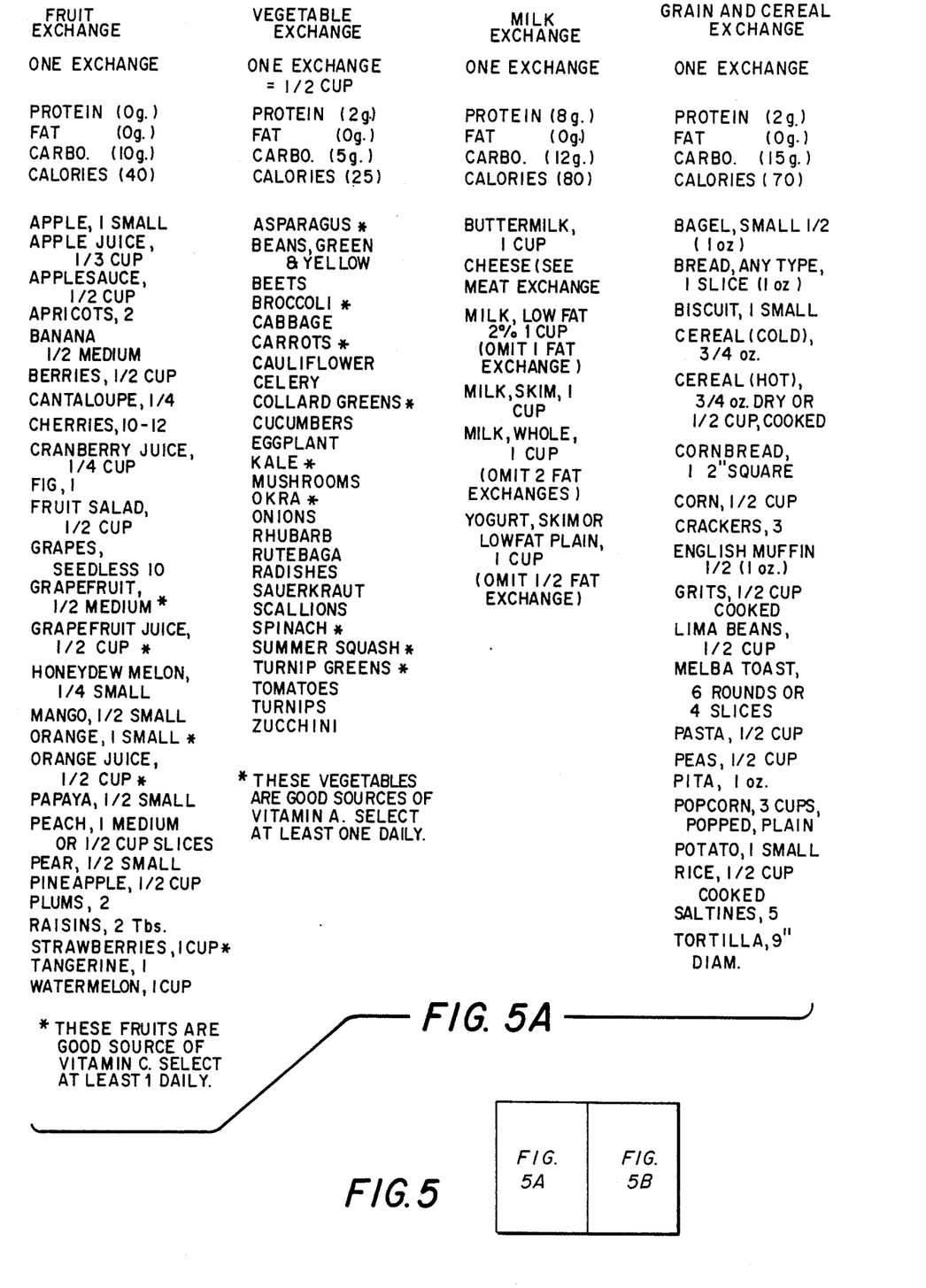
FIG. 5 is a Food Exchange Chart listing food items for different food categories.

At this time various materials 4 are given to the participant with a brief discussion by the dietitian. The materials include a Food Exchange Chart, Daily Meal Plan, Exercise Chart and a seven day journal. The Food Exchange Chart shown in FIG. 5, is the cornerstone of the learning process of what to eat and how much to eat. The chart is a modified version of the American Diabetics Association recommendation which breaks food down into 8 categories. These categories include a fruit exchange, vegetable exchange, milk exchange, grain and cereal exchange, fat exchange, lean meat exchange, medium fat meat exchange, high fat meat exchange. Under each of these categories a wide variety of food items is listed which offers the participant a selection of food items according to their taste preferences. The Daily Meal Plan is shown in FIG. 4. The horizontal rows represent the daily meals within a specified calorie amount. For each meal plan the quantity of food items for each food exchange are indicated in the vertical columns. For example a 1,200 per day meal plan requires for breakfast one food exchange from each of the fruit, milk, grain, fat and milk exchanges It is essential for the weight management system that the participant's meal include the proper quantities from each of the specified food exchanges on the Daily Meal Plan. While the total calorie consumption per day is of major importance, it is essential that these calories be provided from the sources specified in the meal plan. Once the participant has designated a meal plan it is a simple matter to refer to the Food Exchange Chart and select a food item from each of the specified food exchanges. This allows variation and compensation for the participant's food preferences.

The exercise chart provided educates the participant as to what activities should be considered, proper methods of selecting an exercise program and proper procedures of exercising. Additionally, the exercise chart provides training guidelines for increasing one's exercise through a 12 week period. For each week of the training period the exercise chart provides guidelines as to duration and level of physical activity.

The seven day journal given to the participant is to record the amount of food and drink consumed during the day, the manner in which it was prepared and the time at which it was eaten. The purpose of the journal is to provide an accurate and detailed analysis of the past week during a weekly private consultation with the dietitian. In addition, writing down each food item encourages the participant to be aware of the quantities of food consumed during the day.

At this point in the weight loss program the participant begins consultation with a dietitian. Additional material is provided to the participant including a low calorie cookbook, specific cookware, and a seven day menu plan. The cookbook teaches the participant how to cook without the use of additional fats or oils in order to reduce the calorie content of the food. The cookbook in addition offers instructions in cooking without additional water, thereby avoiding loss of vitamins during cooking. Foods prepared without additional fats or water enhances the natural flavor of the foods and are much healthier. The suggested cooking methods improve the flavor of the foods bringing more pleasure to the meal than other known diet programs.

The seven day meal plan provides a nutritionally balanced low calorie menu prepared by trained personnel. The menus provide suggestions for breakfast, lunch, dinner and snacks in three different categories to fit the daily lifestyle of the participant. The menus include suggestions for preparing the meals at home, for eating lunch out and for eating both lunch and dinner out. In each situation the serving suggestions provide a balanced meal of proper proportions supplying necessary nutrients and calories from each of the items on the Food Exchange Chart. Each of these suggested meals to be prepared at home are selected from the above noted cookbook.

Additional measurements 6 taken at this time are of fundamental importance in having a significant psychological impact on the participant. From these measurements the participant is able to readily recognize the need for a change in his eating habits and lifestyle. Throughout the weight loss program these measurements provide evidence of a reduction in size of various parts of the body and in addition to a reduction in weight gives the participant encouragement and confidence that the program is effective. The measurements include the circumference of the arms, waist, hips, chest and fingers.

The next stage in the weight management system involves extensive consultation between the participant and the dietitian. The dietitian, in functional block 7, reviews the computer analysis with the participant in detail, outlining the deficiencies of the old eating habits and diet. This portion of the consultation utilizes the bar graph of FIG. 2 and the comparison chart of FIG. 3 and the Nutrition Analysis Report of FIG. 8. Referring to FIG. 2, the participant for this example has experienced a diet which has provided the recommended daily amounts of vitamins and protein. The analysis further shows that the participant has consumed an excess of calories needed to maintain a reasonable or desired weight. This of course indicates that the participant cannot lose weight until the calorie content in the diet is reduced. The chart further indicates that the participant's diet provides 115% of the recommended daily allowance of calories or an excess of 15%. A similar situation can be seen with the fat intake where the old diet provides 120% of the recommended daily allowance or an excess of 20%. From this graph the participant can have a clear indication that their calorie content needs to be reduced by 20% and the fat content needs to be reduced by 15%. The graph of FIG. 2 further identifies a deficiency in the carbohydrate intake of about 20%. This deficiency is also based on the recommended daily allowance.

The dietitian's consultation 7 further includes a detailed discussion of the comparison chart shown in FIG. 3 produced by the computer analysis. As previously discussed this chart provides a breakdown of the source of calories consumed by the participant. As can be seen in FIG. 3, 25% of the calories consummed are from fat, 10% from protein, 30% from carbohydrates and 35% from alcohol. This analysis is shown in comparison with a breakdown of calorie intake as recommended by the United States Senate Committee.

It is at this time the importance of a properly balanced diet that is stressed. In addition to the proper number of calories consumed it is essential that the calories be provided from specific sources. As shown in FIG. 3, approximately 30% of the calories should be provided from fats, 12% from protein and 58% from carbohydrates. The participant thus ideally needs to reduce the calorie intake from alcohol and proportion the remaining calorie intake among the three remaining groups. It has been found that by showing a comparison chart using the participant's own diet results in a higher interest which in turn makes learning much easier.

Figure 6:
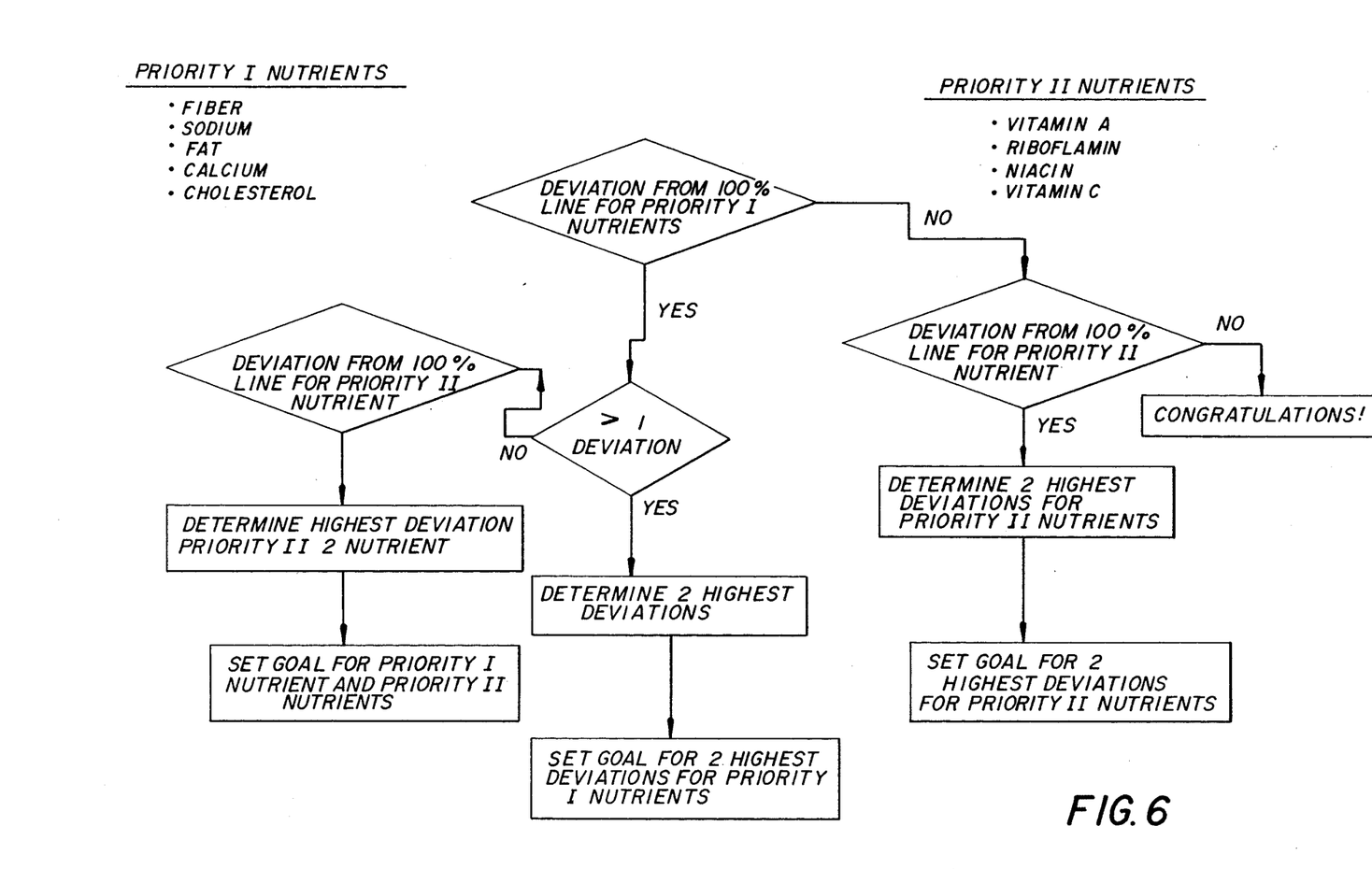
FIG. 6 is a flow diagram of the computer analysis in priority of nutrients.

The weaknesses of the diet are stressed throughout the weight management system and it has proven beneficial to have the participant set goals at this time to correct the deficiencies in the diet. Initially only one weakness is emphasized in the preferred embodiment and normally this weakness is used as the goal for that week. At the end of the week the dietitian reviews the progress and if that one weakness is showing satisfactory improvement, additional goals are set to correct the remaining deficiencies. Normally the deficiencies are corrected one at a time. In order for the dietitian to aid the participant in setting goals the computer analysis calculates at which nutrients a deficiency exists. The flow chart for such an analysis is shown in FIG. 6. The computer classifies the nutrient into two categories identified as Priority I and Priority II nutrients. The Priority I nutrients are the nutrients where the amount taken in must be within a specified range. The human body requires a specified amount of these nutrients to function properly on a daily basis, however, an excessive amount has been shown to have undesirable consequences. The Priority I nutrients for the purposes of this example include, cholesterol, fiber, sodium fat and calcium. The Priority II nutrients are those which, while essential to good health, are not of major concern if the diet periodically does not provide the recommended daily allowance. For the purposes of example only these Priority II nutrients may include vitamin A, riboflavin, niacin and vitamin C. The computer analysis determines whether there is a deviation of any of these Priority I nutrients from the recommended daily allowance. If there is a deviation the computer determines the number of nutrients of which there is a deviation and if there are two or more the computer selects the two nutrients with the highest deviation. From this identification the dietition is able to recommend particular foods to correct the nutrient excess or deficiency. For example, if the analysis indicated the sodium and fat level as being abnormally high the dietition might recommend a reduction in specific types of meat and reducing the intake of salted foods. The two highest deviations would normally be used as the first goals.

If there is only one Priority I nutrient deviation it has been considered not to be of major immediate concern and will normally be corrected by adjusting the overall diet. The computer detecting only one deviation of Priority I nutrients then determines the number of deviation from the recommended daily allowance of the Priority II nutrients. As with the Priority I nutrients the computer identifies the two nutrients having the greatest deviation. From this identification the dietition is able to set goals with the participant to correct the deviation. For example, if the computer determines this is a major deficiency of vitamin C and vitamin A the dietition might recommend a diet concentrating more on green vegetables and citrus fruits.

Simultaneously with the review of the computer analysis 7 a detailed explanation of the Daily Meal Plan and the Food Exchange Chart FIGS. 4 and 5 and an exercise chart are given as indicated by functional block 8. Prior to this time only a general explanation has been offered to the participant as to their use and benefit. From reviewing the Food Exchange Chart and the Daily Meal Plan the participant is able to discover exactly what is causing the deficiencies in their diet and how to correct the situation. The dietitian works with the participant to teach how to select food items from each of the food categories and how to assemble properly balanced and flavorful meals from the Daily Meal Plan in the manner explained above.

In selecting a meal plan it is necessary to determine the number of calories recommended per day in order to lose and maintain a desired weight. The first step is to find the participant's reasonable or desired weight for their height and build. From the height and build the weight is determined based on data prepared by the Metropolitan Insurance Company in 1983, reproduced in FIG. 9. The Handbook of Clinical Dietetics, Yale University Press, provides a formula for determining the maximum calories to be consumed per day necessary to maintain one's weight. This formula multiplies the reasonable weight determined from the chart in FIG. 9 by 11 cal/lb if the person engages in sedentary activity. If the person engages in light activity then the weight is multiplied by 13 cal/lb for moderate activity 15 cal/lb and 20 cal/lb if the person normally engages in strenuous activity. This results in the number of calories needed to maintain the reasonable weight. For example, if the participant has a reasonable weight of 140 lbs. and engages in light activity then the number of calories needed to maintain the reasonable weight is 1,820 per day. If the daily calorie needs fall between the rows of calories in the Daily Meal Plan it is suggested the lower row be selected as most people tend to underestimate meal portions. An additional feature of the computer analysis is a determination whether an intermediate meal plan is in order. For those extremely overweight a drastic reduction in calorie intake is liable to have serious and psychological and emotional consequences which may rapidly discourage the participant and leave the program. For this type of situation an intermediate menu plan is prepared by computer analysis to offer a compromise between the ideal calorie intake level to achieve the desired weight and the calorie intake of the old eating habits. In determining whether an intermediate menu plan is appropriate the computer receives an input of the present weight A, ideal weight B and the activity level C. The activity level is the number of calories needed per pound per day. From this data the computer determines the excess in calories consumed per day D according to the formula:

$$(A \times C) - (B \times C) = D$$

If the excess calories D is greater than 1000 calories per day an intermediate menu plan is recommended. The intermediate menu plan is determined according to a calculated Intermediate Weight rather than from the ideal weight of the participant. The Intermediate Weight is defined by the formula:

$$I = A - \left(\frac{A - B}{2}\right)$$

As an example consider a participant whose actual weight is 220 pounds and has a sedentary activity level (11 cal/day) and a desired or ideal weight of 120 pounds. From the formula the computer determines an excess caloric intake D of:

$$(220 \ lb \times 11 \ cal/lb) - (120 \ lb \times 11 \ cal/lb) = 1100 \ cal$$

The computer determines that the excess in calories D is greater than 1000 and calculates an intermediate weight as follows:

$$I = 220 \ lb - \left(\frac{220 \ lb - 120 \ lb}{2}\right) = 170 \ lbs$$

From this intermediate Weight of 170 pounds the Menu selected which will provide calories to maintain a weight of 170 pounds. Specifically, for sedentary activity the menu plan provides:

$$170 \ lb \times 11 \ cal/lbs = 1870 \ \text{calories per day.}$$

Once the participant has reached 170 pounds a second menu plan is prepared using the ideal weight as outlined above.

No reasonable weight loss program having the objectives of lifetime changes can be effective without a reasonable increase in the physical activity level. The exercise habits 9 are discussed with the participant and the exercise chart is explained as outlined above. At this time an appointment is made for a group exercise session as indicated in block 15.

A seven day journal is given to the participant 10 to record each food item consumed throughout the week. This journal is used in combination with the computer analysis, giving an indication of the strengths and weaknesses of the diet for the entire week. Used in parallel with the food exchange chart it shows what the past weeks would have looked like had the participant known how to use the chart. Each week a new journal is given to the participant to record the progress and changes in behavioral patterns.

The next portion of the weight maintenance system deals with behavior modification. Cooking demonstrations 11 are given for the participant to educate them as to proper techniques of preparing meals. Emphasis is made on discarding old habits which do not induce good nutrition and weight maintenance. It has been found that a simple lecture is not generally an effective teaching method. Actual demonstrations with repetitions have shown to be the only truly effective methods of teaching proper cooking techniques. The demonstrations show the participants that a low calorie meal can be flavorful and is no more difficult to prepare than an unhealthy meal. The recipes prepared are selected from a cookbook provided and the participants are required to try the recipes at home. This requirement proves to the participants that healthy cooking is not additional work and that the entire family will also find the meals flavorful and enjoyable. Acceptance of the meals by the family members offers positive reinforcement to the participants which has proven to be a powerful tool in changing one's lifestyle.

Positive reinforcement is further provided by group sessions 12 between the different participants. Each participant asks questions, exchanges experiences and offers support and encouragement to each other. Discussions about the reactions of family members to the meals prepared offers encouragement to others to try different recipes.

As part of effective behavior modification it is necessary to educate the participants in proper nutrition. Extensive discussions 13 are held in private counseling and in group discussions with other participants emphasizing the need and importance of a well balanced diet in maintaining one's proper weight. Additional literature is offered on general nutritional needs as well as specific categories of nutrients.

As previously discussed, exercise is an essential part of any effective weight management system. At this point in the system 14 a group session is held among the participants by a physiologist on the benefits and attributes of proper exercise. Techniques for proper ways to exercise and the proper amounts of exercise are discussed in detail. Various activities by the individual participants are shared with the others thereby offering encouragement and reinforcement for their goals of managing their weight effectively in a safe and healthy manner. Different exercise programs and activities are discussed and dates are set for these activities. It has been found that for the beginner a firm commitment by the participant is an essential aspect of developing a regular exercise program.

As part of the exercise session 15 a specific activity is scheduled and undertaken by the participants which may for example be a walk. In order to insure attendance the participants were scheduled for the activities during the consultation with the dietitian in block 9. In much the same manner as the cooking demonstrations it has been found that only actual practice and participation will develop sound exercise habits. Simply offering the participants the exercise chart will not be sufficient inducement to exercise but rather it is necessary to get each individual involved.

The walk or other activity is normally scheduled before a group session giving the participants the opportunity to become acquainted with one another. Walking in a group allows encouragement from each other and develops a sense of togetherness. Group exercise programs enable the participant to recognize that exercise can be an enjoyable experience.

For most people the weight management system is a tremendous undertaking which requires support from the participant's family. It has been found that family counseling can be a major factor in the success of the program. When undertaking previous weight loss diets the participant may have received many unpleasant and unencouraging comments from the family. The family members may remember previous diets where the participant was unsatisfied with the results and became irritable and unpleasant to live with. Memories of these difficult experiences by family members is not inducive to the positive reinforcement needed when any change in lifestyle is desired. Effective weight loss and change in lifestyle affects not only an individual but everyone in the participant's environment. Support is necessary from the family members in order to maximize the chances of success.

As the changes in cooking habits are stressed in the program it is necessary to convince the family members to accept these changes. The changes in cooking techniques have an impact on the entire family and it is necessary that the family members recognize the importance and advantages of these changes. An important feature of the family session is to get the family to realize that the participant is on their last weight loss experience. This alone will help the family readily accept the necessary changes.

Cooking seminars 17 are offered which include actual cooking of an entire meal by the participants. Guidance is offered during the session to encourage proper cooking techniques. The groups are generally relatively small which allows the counselor to offer more individual attention. As with exercising it has been found that making an appointment and actual practice is effective in developing the proper techniques.

Weekly consultation is provided to monitor the progress of the participants once they have been educated in the proper cooking and exercise techniques and have learned to effectively use the Daily Meal Plan and the Food Exchange Charts. Weight is monitored weekly 18 to determine the success the participant is experiencing. If the weight loss is unsatisfactory the participant is referred back to the initial consultation to the dietitian. With the dietitian a review is made of the computer analysis 7, the Food Exchange Chart, Daily Meal Plan and exercise chart 8, the participants exercise habits 9 and the seven day journal 10.

Weekly consultation further reviews the cooking experiences 19 and exercise habits 20 using the techniques learned from the weight loss system. The seven day journal 21 is examined to determine progress and changes in eating habits are offered to correct some of the weak areas. New goals 22 are also discussed with a counselor for the coming week. These goals may for instance be additional weight loss, longer exercise or more strenuous exercise or a change in eating habits.

From the weekly consultation the participant is able to go back to reinforce the skills they have learned in the behavior modification and exercise sessions as shown by line 24. Every 10 weeks the participant's measurements are again taken, line 26 of the flow chart in FIG. 1, to indicate progress and offer encouragement.

The above described composite arrangement has thus been shown to provide an improved weight management system. The system provides individualized menu and exercise plans based on the physical profile of the individual, past eating habits, individual taste preferences and the activity level of the individual.

The above described system is merely illustrative of the principles of the present invention. Numerous modifications and adaptations thereof will be readily apparent from those skilled in the art without departing from the spirit and scope of the present invention.

What is claimed is:

1. A method of individualized weight management comprising:

(a) obtaining a medical history of a subject and determining the existence of any physiological abnormalities;

(b) obtaining a present physical profile of said subject said profile including data as to sex, physical measurements for determining frame size such as bone or wrist measurements, weight and height of said subject;

(c) obtaining specific information of recent food items caused by said subject and recent level of physical activity in terms of the number of calories burned per pound or per kilogram per day;

(d) entering data obtained from steps (a)–(c) into a computer for comparison with predetermined standards of food consumption given a specified sex, frame size, weight, height and said recent level of physical activity in terms of the number of calories burned per pound or per kilogram per day in relation to an ideal weight;

(e) obtaining a computer analysis of the comparison of the results of step (d) with the caloric and nutritional requirements for said subject at said ideal weight at said recent level of physical activity and employing said computer to calculate the deviation of the current eating habits from said requirements for said subject;

(f) computing with said computer to determine whether a subject should be placed on an intermediate diet plan having a target weight above an ideal target weight by utilizing the formula:

$$(A \times C) - (B \times C) = D$$

wherein
(a) represents the actual current weight of the subject in pounds or kilograms;
(b) represents the ideal weight in the same unit of measure as A and as determined by said compute analysis;
(c) represents said activity level of said subject in terms of the number of calories burned per pound or per kilogram per day in which said activity level is represented by the values of 11 calories per pound for sedentary activity; the value of 13 calories per pound for light activity; the value of 15 calories per pound for moderate activity and the value of 20 calories per pound for vigorous physical activity;
(d) is a calculated number which if greater than 1,000 calories indicates said subject should be placed on a diet in which said target weight should be initially set above said ideal target weight;
(e) providing said subject with information as to a weight control program in which the eating habits are modified by selectively placing the caloric and nutritional intake at a targeted weight substantially at or above the value corresponding to said ideal weight;
(f) providing said subject with behavior modification instruction to alternatives to past food consumption wherein said behavior modification is selected from the group consisting of cooking, eating, exercise, nutrition or a combination thereof;
(g) providing said subject with periodic goals for achieving said behavior modification;
(h) providing periodic consulation with said subject and review to ascertain the attainment of goals resulting from step (i) and providing additional goals; and (k) following up said consulation and review with periodic computer analysis of said ideal with additional data gathered including the changes in weight and food consumption of said subjects in relation to said predetermined standards.

2. The method of individualized weight management of claim 1 wherein said step of obtaining said medical history includes historical information as to blood pressure, heart anomalies, chronic diseases and pregnancy.

3. The method of individualized weight measurement of claim 2 wherein said step of obtaining said physical profile and said physical measurements for determining frame size comprises the measurement of the circumference of the wrist of said subject.

4. The method of individualized weight measurement of claim 1 wherein said step of obtaining specific information on recent food items consumed includes data on fat, carbohydrate protein and caloric intake in relation to the number of calories burned per pound or per kilogram per day.

5. The method of individualized weight management of claim 1 wherein said step of following up said consultation with additional data includes periodic updating as to changes in nutrient intake of said subject compared with predetermined standards.

6. The method of individualized weight management of claim 5 wherein said step of following up said consultation and review with periodic computer analysis further includes a print-out of the sources of calories consumed.

7. The method of individualized weight management of claim 6 wherein said print-out of said sources of calories consumed includes catagories listing the amounts of protein, carbohydrates, fat and alcohol as separate calorie sources.

8. The method of individualized weight management of claim 1 wherein said step of following up said consultation with additional data includes periodic updating as to changes in the physical activity level of said subject.

9. The method of individualized weight management of claim 1 wherein said step of following up said consultation with additional data includes computer analysis of the sources of calories consumed which are then compared with predetermined standards for sources of calories.

10. The method of individualized weight management of claim 1 wherein said step of obtaining specific information of recent food items consumed by said subject includes information as to past food consumption and data regarding food item preferences.

11. The method of individualized weight management of claim 10 wherein said step of obtaining specific information of recent food items consumed by said subject includes information regarding food item taste preference.

12. The method of individualized weight management of claim 1 wherein said step of behavior modification instruction includes instruction in selecting quantity and types of foods.

13. The method of individualized weight management of claim 1 wherein said step of behavior modification instruction includes instruction for physical exercise.

14. The method of individualized weight management of claim 1 wherein said step of behavior modification includes modifying cooking habits to waterless and greaseless cooking.

15. A weight management method for attaining an ideal weight comprising:

(a) obtaining medical history of a subject to enumerate specific potential physiological abnormalities;

(b) obtaining a physical profile of said subject by means of obtaining data on height, sex, frame size, and weight;

(c) obtaining information as to physical activity level and past food consumption over a specified period of time in terms of types of food, nutritional value, and the number of calories burned per pound per day;

(d) inputting data obtained from the information obtained in steps (a)-(c) to a computer for comparison with predetermined standards;

(e) ascertaining the number of calories said subject is above an ideal calorie and nutritional intake level;

(f) obtaining a computer analysis of the current calorie and nutritional level of said subject in relation to said predetermined standards;

(g) providing an intermediate calorie level above said ideal calorie and nutritional intake level for a predetermined period of time where the number of calories said subject is above said ideal calorie and nutritional level is greater than 1000 calories;

(h) providing said subject with information as to a modification of eating patterns to selectively place said subject either at said ideal calorie and nutritional level, above said ideal calorie and nutritional intake level, or not more than 300 calories below said ideal calorie and nutritional level:

(i) providing said subject with behavior modification instruction to alternatives to past food consumption wherein said behavior modification includes one or more changes selected from the group consisting of cooking, eating, nutritional and exercise habits;

(j) providing said subject with goals for achieving behavior modification on a periodic basis;

(k) providing periodic consultation and review with said subject to ascertain the attainment of goals of step (h) and providing additional goals; and (l) following-up the consultation and review with a further computer analysis of the present weight and food consumption of said subject in relation to said predetermined standards.

16. The weight management method of claim 15 wherein said step of ascertaining the number of calories said subject is above said ideal calorie and nutritional intake level is calculated by said computer.

17. The weight management method of claim 16 wherein said step of obtaining information as to physical activity level and past food consumption includes obtaining information as to food taste preference.

18. The weight management method of claim 15 wherein said step of behavior modification includes modifying at least one member of the group consisting of cooking, eating and exercise habits.

19. The weight management method of claim 18 wherein said step of modifying said cooking habits includes greaseless and waterless cooking.

20. The weight management method of claim 15 wherein said step of behavior modification consists of changing exercise habits.

21. The weight management method of claim 15 wherein said step of obtaining information as to physical activity level and past food consumption includes listing amounts of protein, carbohydrates, fat and alcohol as separate calorie sources in relation to the number of calories burned per pound per day.

* * * * *